(12) United States Patent
Gannoe et al.

(10) Patent No.: US 7,033,384 B2
(45) Date of Patent: Apr. 25, 2006

(54) STENTED ANCHORING OF GASTRIC SPACE-OCCUPYING DEVICES

(75) Inventors: James Gannoe, Redwood City, CA (US); Federico Gutierrez, Pacifica, CA (US)

(73) Assignee: Satiety, Inc., Palo Alto, CA (US)

( * ) Notice: Subject to any disclaimer, the term of this patent is extended or adjusted under 35 U.S.C. 154(b) by 180 days.

(21) Appl. No.: 10/233,236

(22) Filed: Aug. 30, 2002

(65) Prior Publication Data

US 2004/0044357 A1 Mar. 4, 2004

(51) Int. Cl.
*A61F 2/06* (2006.01)

(52) U.S. Cl. ............ 623/1.11; 606/194; 604/509; 128/898

(58) Field of Classification Search ........ 606/192, 606/194, 154; 623/1.11; 128/898; 604/509
See application file for complete search history.

(56) References Cited

U.S. PATENT DOCUMENTS

| | | | |
|---|---|---|---|
| 3,986,493 A | 10/1976 | Hendren, III | |
| 4,133,315 A | 1/1979 | Berman et al. | |
| 4,246,893 A | 1/1981 | Berson | |
| 4,402,445 A | 9/1983 | Green | |
| 4,416,267 A * | 11/1983 | Garren et al. | 128/898 |
| 4,485,805 A * | 12/1984 | Foster, Jr. | 128/898 |
| 4,598,699 A | 7/1986 | Garren et al. | |
| 4,607,618 A | 8/1986 | Angelchik | |
| 4,641,653 A | 2/1987 | Rockey | |
| 4,648,383 A | 3/1987 | Angelchik | |
| 4,694,827 A | 9/1987 | Weiner et al. | |
| 4,723,547 A | 2/1988 | Kullas et al. | |
| 4,739,758 A | 4/1988 | Lai et al. | |
| 4,773,393 A | 9/1988 | Haber et al. | |
| 4,899,747 A | 2/1990 | Garren et al. | |
| 4,969,474 A | 11/1990 | Schwarz | |
| 5,059,193 A | 10/1991 | Kuslich | |
| 5,084,061 A | 1/1992 | Gau et al. | |
| 5,112,310 A | 5/1992 | Grobe | |
| 5,129,915 A | 7/1992 | Cantenys | |
| 5,234,454 A | 8/1993 | Bangs | |
| 5,259,399 A | 11/1993 | Brown | |

(Continued)

FOREIGN PATENT DOCUMENTS

EP 0 246 999 A1 11/1987

(Continued)

OTHER PUBLICATIONS

T. M. Boyle et al., "Small Intestinal Obstruction Secondary to Obturation by a Garren Gastric Bubble", *The Am. J. of Gastroenterology*, vol. 82, No. 1, 1987, pp. 51-53.

(Continued)

*Primary Examiner*—Glenn K. Dawson
*Assistant Examiner*—Darwin P. Erezo
(74) *Attorney, Agent, or Firm*—Fulwider Patton LLP

(57) ABSTRACT

Gastric space occupying devices are provided that include a stent configured for deployment in the gastrointestinal tract of a patient, and in particular, for deployment in the esophagus or the stomach. Secured to the stent is an expandable member that is adapted to reside within the patient's stomach. When expanded, the expandable member occupies a predefined volume within the patient's stomach and is further tethered to the deployed stent, thereby retaining or anchoring the expandable member within the stomach. Methods and systems for the deploying the space occupying devices are also provided.

8 Claims, 2 Drawing Sheets

U.S. PATENT DOCUMENTS

| | | | |
|---|---|---|---|
| 5,330,486 | A | 7/1994 | Wilk |
| 5,334,210 | A | 8/1994 | Gianturco |
| 5,411,408 | A | 5/1995 | Bessler et al. |
| 5,555,898 | A | 9/1996 | Suzuki et al. |
| 5,792,153 | A | 8/1998 | Swain et al. |
| 5,868,141 | A | 2/1999 | Ellias |
| 5,876,448 | A | 3/1999 | Thompson et al. |
| 5,902,333 | A * | 5/1999 | Roberts et al. ............ 606/191 |
| 5,935,107 | A | 8/1999 | Taylor et al. |
| 5,993,473 | A | 11/1999 | Chan et al. |
| 6,013,854 | A * | 1/2000 | Moriuchi ................. 623/1.11 |
| 6,030,364 | A | 2/2000 | Durgin et al. |
| 6,136,006 | A | 10/2000 | Johnson et al. |
| 6,200,318 | B1 | 3/2001 | Har-Shai et al. |
| 6,248,058 | B1 | 6/2001 | Silverman et al. |
| 6,454,785 | B1 * | 9/2002 | De Hoyos Garza ......... 606/192 |
| 6,464,625 | B1 * | 10/2002 | Ganz .............................. 600/3 |
| 6,506,202 | B1 * | 1/2003 | Dutta et al. ................. 606/194 |
| 6,675,809 | B1 * | 1/2004 | Stack et al. ................. 128/898 |
| 6,773,441 | B1 | 8/2004 | Laufer |
| 6,835,200 | B1 | 12/2004 | Laufer et al. |
| 2001/0037127 | A1 | 11/2001 | De Hoyos Garza |
| 2004/0162568 | A1 | 8/2004 | Saadat et al. |
| 2004/0225183 | A1 | 11/2004 | Michlitsch et al. |

FOREIGN PATENT DOCUMENTS

| | | |
|---|---|---|
| JP | 63277063 A | 11/1988 |
| JP | 63279854 | 11/1988 |
| JP | 63302863 A | 12/1988 |
| JP | 01049572 A | 2/1989 |
| JP | 04297219 | 10/1992 |

OTHER PUBLICATIONS

C. Clark, "The Gastric Bubble: Medicine, Magic or Mania?", *SGA J.*, vol. 9, No. 2, 1986, 45-47.

S. L. Edell et al., "Radiographic Evaluation of the Garren Gastric Bubble," *AJR* 145, 1985, pp. 49-50.

S. Gukovsky-Reicher, M.D. et al., "Expandable Metal Esophageal Stents: Efficacy and Safety", Review of Current Literature Data and of 53 Stents Placed at Harbor-UCLA Medical Center, www.medscape.com/viewartcle, 20 pgs. downloaded Aug. 24, 2002.

D. F. Kirby et al., "Incomplete Small Bowel Obstruction by the Garren-Edwards Gastric Bubble Necessitating Surgical Intervention", *The Am. J. of Gastroenterology*, vol. 82, No. 3, 1987, pp. 251-253.

O. G. Nieben et al., "Intragastric ballon as an artificial bēzoar for treatment of obesity", The Lancet, Mar. 27, 1982, pp. 198-199.

T. V. Taylor et al., "Gastric Baloons for Obesity", The Lancet, Mar. 27, 1982, p. 750.

W. L. Percival, MD, "The Balloon Diet: a Noninvasive Treatment for Morbid Obesity. Preliminary Report of 108 Patients", *The Canadian J. of Surgery*, vol. 27, No. 2, 1984, pp. 135-136.

Y. Vandenplas et al., "Intragastric balloons in adolescents with morbid obesity", *European J. of Gastroenterology & Hepatology*, vol. 11, No. 3. pp. 243-245.

B. De Waele, MD et al., "Inragastric Balloons for Preoperative Weight Reduction", *Obesity Surgery*, 10, pp. 58-60.

S. B. Benjamin et al., Abstract, "A Double-Blind Cross Over Study of the Garren-Edwards Anti-Obesity Bubble", *Gastrointestinal Endoscopy*, 1987, Abstract No. 105, vol. 33, No. 2, 1987, p. 168.

S. B. Benjamin, Abstract, "Small Bowel Obstruction and the Garren-Edwards Bubble: Lessons to be Learned?", *Gastrointestinal Endoscopy*, Abstract No. 161, vol. 33, No. 2, 1987, p. 183.

O. W. Cass, Abstract, "Long-Term Follow-Up of Patients with Percutaneous Endoscopic Gastrostomy", *Gastrointestinal Endoscopy*, Abstract No. 162, vol. 33, No. 2, 1987, p. 183.

* cited by examiner

STENTED ANCHORING OF GASTRIC SPACE-OCCUPYING DEVICES

FIELD OF THE INVENTION

The present invention relates generally to medical apparatus and methods and more particularly to devices and methods for the insertion and securing of expandable devices and the like within a patient's stomach, intestine or gastrointestinal tract for purposes of taking up space to provide the patient with a feeling of satiety or fullness. These devices may also be removed once they have served their purpose, e.g., the patient has lost the directed or desired amount of weight.

BACKGROUND OF THE INVENTION

Currently, in cases of severe obesity, patients may undergo several types of surgery either to tie off or staple portions of the large or small intestine or stomach, and/or to bypass portions of the same to reduce the amount of food desired by the patient, and the amount absorbed by the intestinal track. Procedures such as laparoscopic banding, where a device is used to "tie off" or constrict a portion of the stomach, or the placement of intragastric balloons within the stomach can also achieve these results.

Endoscopic procedures that have been used to assist weight loss have been primarily focused on the placement of a balloon or other space occupying device in the patient's stomach to fill portions of the stomach to provide the patient with the feeling of fullness, thereby reducing food intake. To accomplish these procedures, an endoscope is utilized to guide the balloon through the patient's mouth and down the esophagus to the stomach. Usually these procedures have allowed placement of the device for 6–12 months, and are coupled with counseling and other types of psychological support.

In the case of laparoscopic banding or balloon placement, however, several complications can arise that make these procedures, in their present form, clinically suboptimal. The surgical interventions described above require the patient to submit to an intervention under general anesthesia, and can require large incisions and lengthy recovery time. The less invasive procedures described above, although clinically efficacious in many cases, suffer from complications ranging from deflation of the devices resulting in unsustained weight loss, to stomach erosion, bowel obstruction and even death.

Many of these described problems have stemmed from the fact that the devices were not robust enough to sustain long term implantation, and that they were implanted in such a manner as to remain unattached or free-floating within the stomach. Further, due to the caustic nature of stomach acids and other factors, many of the implants deflated and migrated into the intestine, causing bowel obstructions and in some cases death. Also, many devices were not well designed for removal, leading to additional technical difficulties for the clinician.

BRIEF SUMMARY OF THE INVENTION

The present invention provides for improved methods and apparatus for deploying and securing space-occupying devices within the gastrointestinal system of a patient, especially the stomach of the patient, in a minimally invasive manner such as through transesophageal endoscopy. The invention allows greater access to procedures and devices by patients who might not otherwise be treated surgically as "morbidly obese" (at or above a Body Mass Index (BMI) of 40 kg/m3), but who may just be moderately obese or overweight (BMI of between 25 to 40 kg/m3). In addition, patients who require more invasive surgery for an unrelated ailment, may need a minimally invasive way to lose the weight prior to their more invasive procedure, thereby reducing the risks associated with general anesthesia, or otherwise enabling the more invasive procedure.

In particular, the present invention provides for space occupying devices that include a stent configured for deployment in the gastrointestinal tract of a patient, and in particular, for deployment in the esophagus or the stomach. Secured to the stent is an expandable member that is adapted to reside within the gastrointestinal tract and, especially, within the patient's stomach. When expanded, the expandable member occupies a predefined volume within the patient's stomach or gastrointestinal tract.

The present invention also provides for methods and systems for the deploying such space occupying devices.

DETAILED DESCRIPTION OF THE INVENTION

The present invention provides for space occupying devices having an expandable, space-occupying member tethered to an anchoring stent. The stent itself is typically of the self-expanding variety that can be easily deployed within, e.g., a patient's esophagus or stomach, and remain in a generally fixed relationship relative to the patient's stomach cavity. The expandable member is tethered to the stent in a manner allowing the expandable member to reside within the patient's stomach. This system has certain advantages over other known systems, including allowing for a much less traumatic method of anchoring or otherwise retaining the expandable member within the stomach as compared to other systems. For example, methods described in U.S. patent application Ser. No. 09/816,850, filed Mar. 23, 2001, which is commonly owned is and incorporated herein by reference in its entirety, rely on the use of suture or other fastening means that penetrate the stomach wall to anchor an expandable device to the stomach wall. The present invention by contrast avoids compromising the integrity of the stomach wall or gastrointestinal tract in general.

Figure 1:
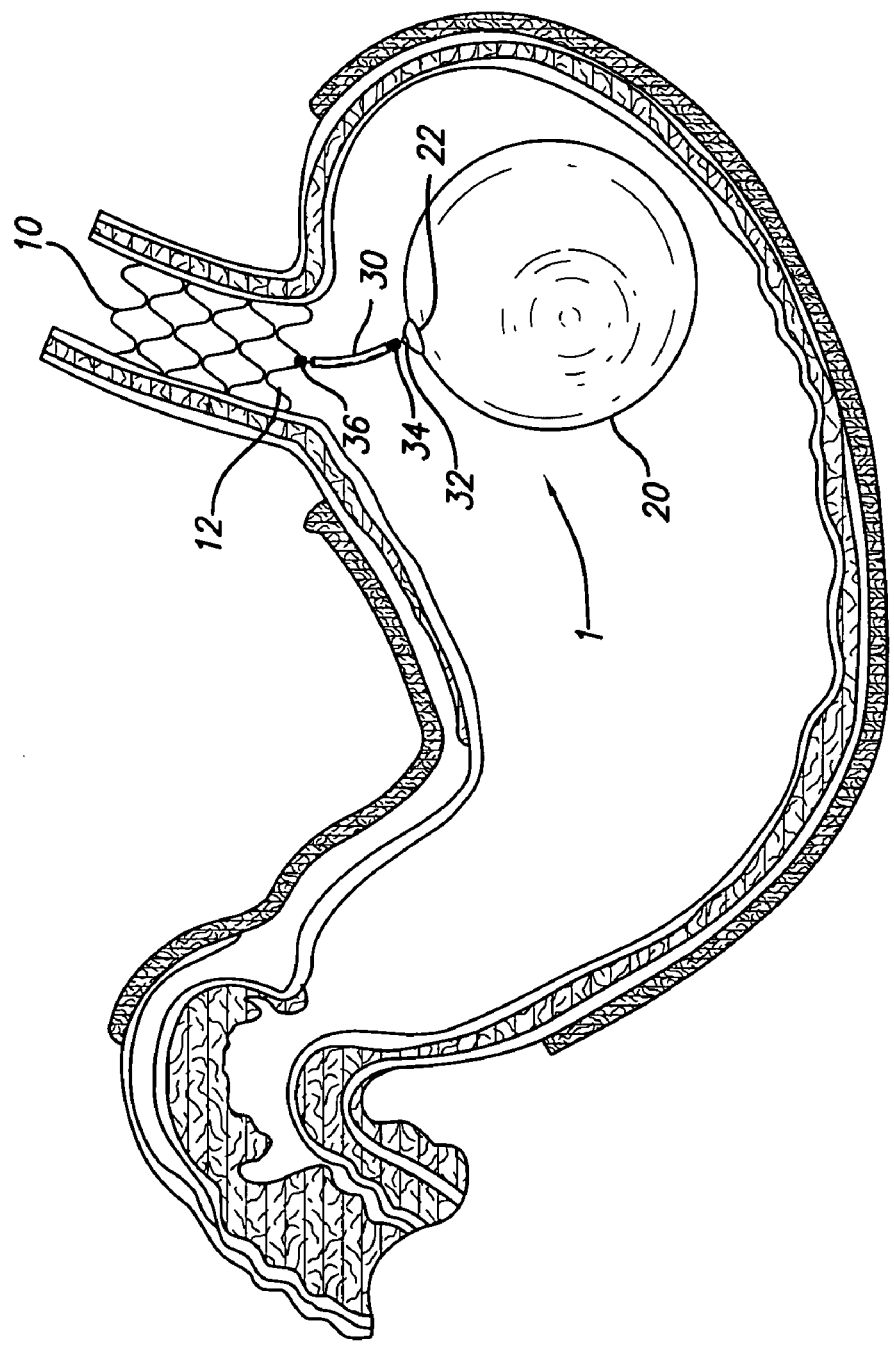
FIG. 1 shows a cross-sectional view of the esophagus and stomach of a patient, with a space occupying device according to the present invention deployed therein, the stent portion of the device being deployed and anchored against the esophagus and the expandable member portion secured to the stent portion and residing within the stomach.

Referring now to FIG. 1, an embodiment of a space occupying device 1 according to the present invention is depicted having anchoring stent 10 and expandable member 20. As shown, anchoring stent 10 is deployed within the esophagus, remaining in a fixed location relative to the stomach. Tether 30 is secured to both anchoring stent 10 and expandable member 20, connecting the two together. Expandable member 20 includes tethering region 22 in the form of a ring or a clasp integral to the member. Distal end 32 of tether 30 is attached to tethering region. Proximal end 36 of tether 30 is attached to anchoring stent 10 at distal end 12 of the anchoring stent. Tether 30 further includes swivel portion 34 located proximal of distal end 32. Swivel portion 34 allows the expandable member to twist or rotate freely without transmitting torque or other rotational forces onto anchoring stent 10. Tether 30 can also be configured with a swivel, rotating joint, or other similar mechanism at proximal end 36 of tether 30 to further relieve torque or rotational strain on stent 10 due to twisting or rotation of expandable member 20.

Stent 10 can be formed in a variety of configurations and of a variety materials known to one skilled in the art. In particular, conventional esophageal stents can be used or readily modified for use in the present invention. Such stents can be of the non-expanding or expanding variety, including those typically used in addressing problems of progressive dysphagia associated with esophageal cancer. Expanding stents include those that are deformable and that are typically expanded using, e.g., a balloon catheter, as well as those that are resilient in nature and that can be delivered in a compressed state and which can self-expand to their original state. Preferably, the stents are of the radially self-expanding variety for ease of deployment in the esophagus. Typically, such stents are made of stainless steel or nitinol (nickel-titanium alloy) and formed into e.g. knitted wire tube, tubular mesh, coiled spring, and like configurations. Suitable self-expanding esophageal metal stents (SEMS) include those sold under the brand names Esophacoil™ (Medtronic/Instent, Eden Prairie, Minn.), Ultraflex™ (Boston Scientific/Microvasive, Natick, Mass.), Wallstent™ (Boston Scientific/Microvasive, Natick, Mass.), and Z-stent™ (Wilson-Cook, Winston-Salem, N.C.). Additional examples of such stents include those described in U.S. Pat. Nos. 5,876,448 and 6,248,058, each of which is incorporated herein by reference in its entirety. Length and diameter of the stent can usually range from 6–15 cm (length) and 16–22 mm (diameter) for most applications. The stents may further be coated, either partially or completely, with e.g. a polymeric film such as silicone.

Expandable member 20 is an inflatable balloon and may be formed of a urethane interior and a silicone exterior. The urethane provides a durability to the balloon for resisting undesirable rupture or leakage and the silicone exterior provides for a smoothness, and conformability to avoid unnecessary trauma or irritation to the stomach lining. In another variation, the expandable member 20 is formed of a composite of silicone, aluminized polyester film, and polyethylene. In this variation, the space occupying device is formed by heat-sealing sheets of mylar/polyethylene composite. The seam is then trimmed to a minimum size and a valve attached. The assembly is then dipped in room temperature vulcanizing (RTV) liquid silicone which, once cured, will leave a smooth surface, which may or may not have a palpable seam. Alternatively, the space occupying device can be rotated as the silicone cures, to allow for a more consistent coating to form. In yet another variation, the balloon is formed of weldable polyolefin films. A variety of sizes and shapes of space-occupying member 30 are contemplated, and it is to be appreciated that one skilled in the art would be competent to choose a particular shape and size according to the particular application. The space-occupying member 30 can be, for example, a spherical or ellipsoidal balloon or another suitable shape. In the case of an ellipsoidal balloon, one method of anchoring such a balloon is along the longer axis of the balloon; however, anchoring may also be achieved by anchoring along the shorter axis of the balloon. Balloon volumes can vary, but a typical volume is approximately 500 cubic centimeters (cc).

Other types of expandable members capable of occupying space within the stomach are also contemplated for use in the present invention. These include, but are not limited to, expandable members such as those described in U.S. patent application Ser. No. 09/816,850, incorporated herein by reference, which include expandable members that can be expanded upon introduction of inflation media or other materials, or through other means including mechanical expansion means. In addition, the expandable member may further incorporate or include materials or markers such that the expandable member is visible under X-ray or other imaging means. Further, the expandable member may include additional surface features, such as a flange, beads, loops, and/or tabs incorporated into the expandable member to facilitate insertion, manipulation, deflation and/or removal of the expandable member.

Tether 30 can be formed of any suitable biocompatible, nonadsorbable material with sufficient strength to withstand the load placed on it by the expandable member. Such materials include, e.g., conventional suture materials, including stainless steel, silk, nylon, polypropylene, and PTFE. The fasteners and swivels provided on the tether can be formed of e.g. stainless steel or a biocompatible plastic.

Deployment of space occupying device 1 can be accomplished by advancing the expandable member 20 into the patient's stomach, and either concurrently or separately deploying the stent 10. For example, an endoscope or like device can be used pass the expandable member 10, in its deflated state, transorally through the patient's mouth and down the esophagus into the patient's stomach (a transesophageal approach). The same delivery device or a separately introduced device can be used to deliver inflation media (e.g., inert gases, such as air, nitrogen, or fluids such as water, saline, etc.) to expand the member to its desired volume. A less desirable method for introducing expandable member 10 into the stomach would be through a percutaneous gastrostomy procedure to create a gastric fistula through which the deflated expandable member could be passed into the stomach and then inflated. These methods are described in further detail in U.S. patent application Ser. No. 09/816,850, which is commonly owned and incorporated herein by reference.

Stent 10 can be deployed according to conventional methods. Rigid or semi-rigid non-expanding stents usually require dilation of the esophagus prior to placement of the stent. Expandable stents that are deformable but non-self expanding are typically deployed through the use e.g. of a balloon catheter that can expand the stent and deploy it in the desired location against the esophageal wall. Resilient or self-expanding stents are usually delivered to the desired location in a radially compressed state. For example, the stent may be introduced into esophagus on a stent delivery device having an outer tube surrounding the stent that maintains the stent in a radially compressed state. Once positioned at the desired location, the outer tube is axially withdrawn, allowing the stent to radially self-expand. An example of such a device is described in U.S. Pat. No. 5,876,448, incorporated herein by reference in its entirety.

Where the expandable member and stent are separately deployed, tether 30 can be coupled to either the expandable member or the stent prior to their deployment. Additional tools deliverable e.g. through an endoscope, such as graspers or snares, can be used to manipulate the tether and engage it at the desired location on the other element, i.e., either stent or expandable member. Alternatively, the tether itself can be configured with a separate connectable element such that the tether is divided into two portions, one of each being attached to either the stent or the expandable member. Once the stent and expandable member are deployed, a grasper, snare, or other tool can used to manipulate the two tether portions to connect them together.

In a particular method of deployment, a single delivery device is used that is capable of simultaneously deploying both the expandable member and the stent. For example, an endoscope or similar device can be configured to retain both an expandable member in its deflated state and a self-expanding stent in its radially compressed state. This can be accomplished, e.g., by the provision of an overtube that extends over the radially compressed stent and that also extends distally of the endoscope to provide a cavity for the deflated expandable member to reside. The endoscope can be advanced transorally through the esophagus to the stomach at which point the overtube can be partially retracted, deploying the expandable member in the stomach. The endoscope can then be manipulated to position the stent in the desired location in the esophagus and the overtube further retracted to release the stent and permit it to radially self-expand into position. As further described in U.S. patent application Ser. No. 09/816,850, which is commonly owned and incorporated herein by reference, an inflation tube may be further provided culminating in e.g. an inflation needle received through a corresponding valve on the expandable member. The inflation tube can be passed through e.g. a lumen located in the delivery device. In this manner, the expandable member can be inflated upon deployment in the stomach.

Once a patient has lost the desired amount of weight, or based on other determining factors, the inflated expandable member can be deflated and removed according to ways such as those described in U.S. patent application Ser. No. 09/816,850, which is commonly owned and incorporated herein by reference. If desired, the stent can also be removed according to known methods. It may in some cases be advantageous to cut or break the tether prior to removal.

Figure 2:
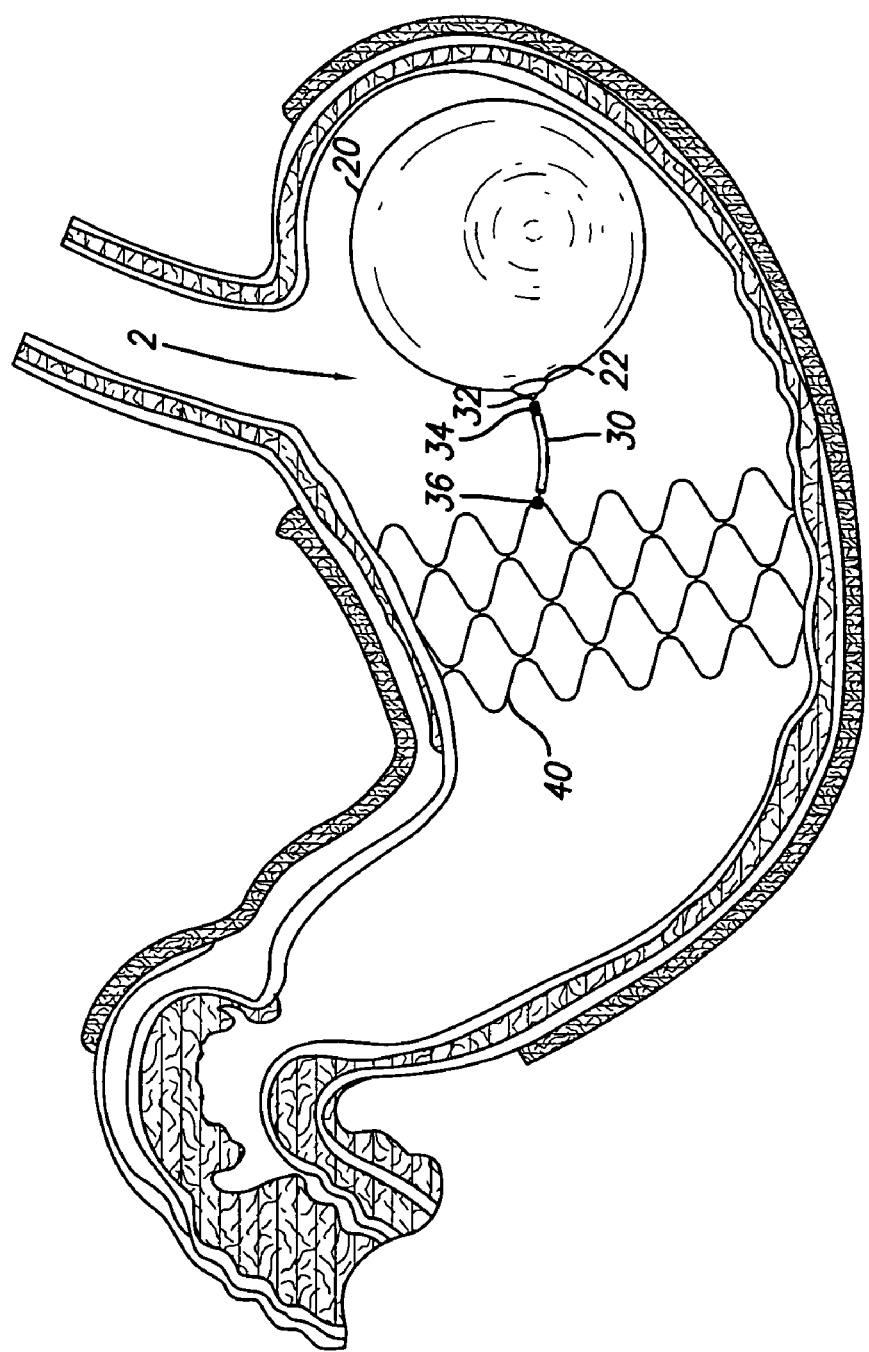
FIG. 2 shows a cross-sectional view of the esophagus and stomach of a patient, with a space occupying device according to the present invention deployed therein, the stent portion of the device being deployed and anchored against the stomach and the expandable member portion secured to the stent portion and residing within the stomach.

FIG. 2 shows another embodiment of the present invention. Space occupying device 2 includes anchoring stent 40 with, expandable member 20 is secured to anchoring stent 40 through tether 30. As can be seen, the embodiment of FIG. 2 is similar to that of FIG. 1 except with anchoring stent 40 being adapted to be deployed and reside within the stomach itself. Stent 40 is preferably an expandable or self-expandable stent of similar construction to that described above with respect to stent 10, but with an expanded diameter the and necessary strength to be positioned and retained within the stomach. The stent can be placed according to ways previously described using a delivery device advanced transesophageally to the desired location in the stomach. Alternatively, the stent can be placed by using percutaneous gastrostomy procedures to create a gastric fistula through which the stent may be passed.

In the embodiments shown in FIGS. 1 and 2, the expandable member is depicted as being located in a spaced apart relationship from the stent. One skilled in the art will appreciate that by adjusting the length of the tether, the location along the stent where the tether is attached, and the particular configuration of the expandable member, one can also achieve orientations of the expandable member where the expandable member is partially, or even fully, disposed within the volume defined by the stent.

Although certain illustrative variations of the present invention are described above, it will be evident to one skilled in the art that various changes and modifications may be made without departing from the invention, and the invention is not intended to be limited by the specifics of any particular variation but is rather defined by the accompanying claims.

I claim:

1. A method of anchoring a space occupying device within a patient's stomach, comprising:
 implanting a stent in the esophagus or stomach of the patient;
 deploying an expandable member in the patient's stomach spaced apart from the stent, the expandable member having a wall defining a sealed volume; and
 attaching the expandable member to the stent.

2. The method of claim 1 wherein the stent is implanted in the patient's esophagus.

3. The method of claim 1 wherein the stent is implanted in the patient's stomach.

4. The method of claim 1 wherein the expandable member is secured to the stent prior to implanting the stent.

5. The method of claim 1 wherein the expandable member is secured to the stent prior to implanting the expandable member.

6. The method of claim 1 wherein the stent is a self-expanding stent.

7. The method of claim 1 wherein the expandable member is inflatable.

8. The method of claim 7 further comprising inflating the expandable member after deployment.

* * * * *